United States Patent [19]
Hatje

[11] Patent Number: 4,930,505
[45] Date of Patent: Jun. 5, 1990

[54] METHOD OF ENHANCING THE WELL-BEING OF A LIVING CREATURE

[75] Inventor: Guenther H. Hatje, Hamburg, Fed. Rep. of Germany

[73] Assignee: Helmut K. Pinsch GmbH & Co., Hamburg, Fed. Rep. of Germany

[21] Appl. No.: 105,608

[22] Filed: Oct. 5, 1987

[30] Foreign Application Priority Data

Oct. 4, 1986 [EP] European Pat. Off. ......... 86113792.5

[51] Int. Cl.$^5$ ............................................. A61N 5/00
[52] U.S. Cl. ........................................ 128/398; 606/3
[58] Field of Search ............... 128/395, 396, 397, 398, 128/303.1

[56] References Cited

U.S. PATENT DOCUMENTS

| | | | |
|---|---|---|---|
| 4,564,012 | 1/1986 | Shimada et al. | 128/395 |
| 4,573,465 | 3/1986 | Sugiyama et al. | 128/395 |
| 4,724,835 | 2/1988 | Liss et al. | 128/303.1 |

FOREIGN PATENT DOCUMENTS

| | | | |
|---|---|---|---|
| 0143185 | 6/1985 | European Pat. Off. | |
| 2458272 | 2/1981 | France | 128/395 |
| 2571264 | 4/1986 | France | 128/395 |
| 2577425 | 8/1986 | France | |
| 1102614 | 7/1984 | U.S.S.R. | 128/395 |
| 1242188 | 7/1986 | U.S.S.R. | 128/395 |
| 8606642 | 11/1986 | World Int. Prop. O. | |

Primary Examiner—Edward M. Coven
Assistant Examiner—Mark J. Graham

[57] ABSTRACT

A method of enhancing the well-being of a living creature, wherein energy from a laser light-source bombards a target area on the skin or hide of the living creature, a short-pulsed laser light source is disposed remote from the target area and produces an elevated emergence energy density so that its radiation, for a short duration, applies a high output per unit area to the target area.

8 Claims, 2 Drawing Sheets

METHOD OF ENHANCING THE WELL-BEING OF A LIVING CREATURE

BACKGROUND OF THE INVENTION

The present invention relates to a method of enhancing the well-being of a living creature, particularly by bombarding a target area on the skin or hide of a living creature with particles originating from a laser light source. The invention is also directed to a laser suitable for use in the method.

It is known to effect the processing of various materials with laser light sources employed for peaceful purposes. It is thus possible, by way of example, to drill very fine and exact holes into the most widely varied materials. In addition, it is possible to utilize laser light sources for spot welding. Such laser light sources must possess a comparatively high power output in order to effect the requisite heating of the material in question.

Furthermore, it is also known to enhance the well-being of human beings or animals with the aid of low-capacity lasers. For this purpose a plurality of individual lasers arranged side-by-side and having a low capacity are employed. This array of laser light sources is brought into the immediate vicinity of the target area. There the effect of the laser radiation engenders a pleasant sensation of warmth or heat. It is alleged that, more particularly horses, by way of example during the regeneration phase subsequent to an injury having been suffered—can be brought back more quickly to top performance by repeated daily applications of such laser radiation. In this known method for stepping up the performance it is of advantage for the laser light source to be brought into relatively close contact with the target area. Measures of this type often upset the well-being of some creatures, particularly relatively highly-strung, top-performance horses, so that the reverse of the desired effect occurs.

SUMMARY OF THE INVENTION

The present invention resolves the technical problem of providing a method for enhancing the well-being of living creature of the kind mentioned in the beginning which works faster and more effectively and is conducive to enhancing the well-being within the shortest period of time possible.

For the solution of the technical problem a method is proposed according to which the laser light source is disposed according to the invention remote from the target area and that a particularly short-pulsed, inter alia even ultrashort-pulsed laser light source with an elevated emergence energy density be employed in such a way that the radiation of the laser light source, for a brief duration, applies a high output per unit area of the target area to the target area. Further advantageous developments result from the subclaims.

Because the laser light source does not have to be located within the proximity of the living creature, thus by way of example, the horse, it is possible to dispose the light source in such a fashion that it is not noticed. It is true that it is known that the transmission of heat produces a pleasurable sensation. However, horses in particular react in an annoyed manner when a technical apparatus is brought into contact with them.

BRIEF DESCRIPTION OF THE DRAWINGS

These and other features of the invention are pointed out in the claims. Other objects and advantages of the invention will become evident from the following detailed description when read in light of the accompanying drawings.

In the drawings.

DESCRIPTION OF PREFERRED EMBODIMENTS

Figure 1:
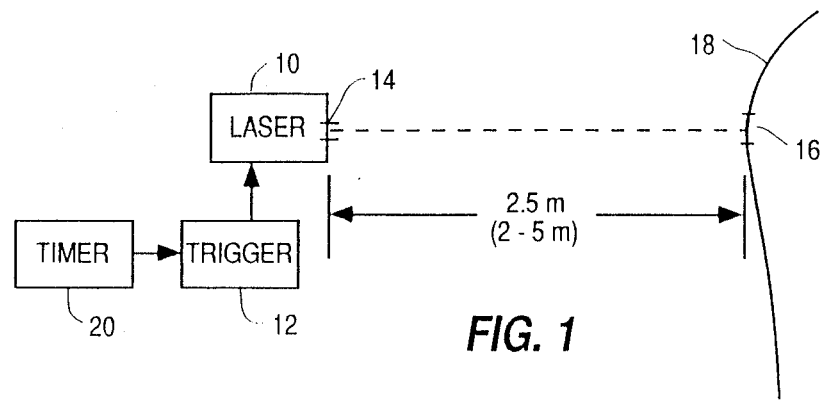
FIG. 1 is a schematic diagram of a system embodying features of the invention.
Figure 2:
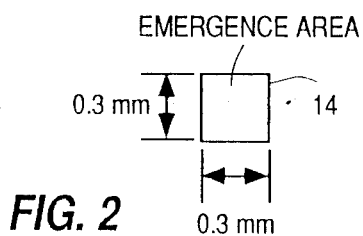
FIG. 2 is a schematic diagram of the emergence area of a laser in FIG. 1.

In FIG. 1, a laser 10 produces an output of 100 watts. A trigger 12, which may form part of the laser 12 or may be outside the laser 12, triggers pulses of extremely short durations, namely, by producing triggering current pulses having a duration of only ten to fifteen ns. The laser 10 possesses an emergence area 14 of $0.3 \times 0.3$ $mm^2$ as shown in FIG. 2. A target area 16 on an animal 18 was set to 10 $mm \times 10$ mm., using the natural divergence of the laser beam, at a distance such as 2.5 meters between the laser 10 light source and the target area. Other distances may be used depending on the divergence of the laser beam. A timer 20 determines the exposure duration of the treatment.

Figure 3:
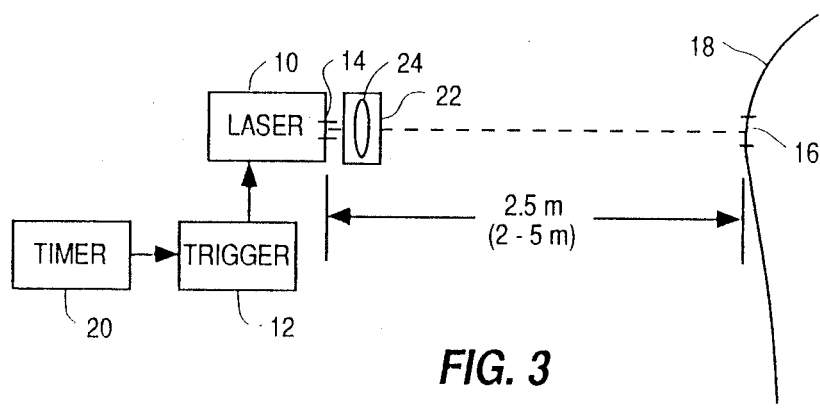
FIG. 3 is a schematic diagram of another system embodying features of the invention.

FIG. 3 illustrates another embodiment of the invention. Here, the laser 10, the trigger 12, and the timer 20 correspond to those in FIG. 1. However, an optical system 22 with a convex lens 24 at the emergence area 14 of the laser 10 sets the target area at 10 mm $\times$ 10 mm at a distance of 2.5 meters between the laser light source and the target area. In this embodiment, the laser 10 and the optical system 22 with its convex lens 24 distribute the radiation completely uniformly within the target area 16. The timer 20 produces an exposure duration of approximately one to two minutes. The laser 10 produces a wave length of 904 nm at 1.04 eV. When used, a one-minute radiation on the target area 16 did not lead to any appreciable rise in temperature at these levels.

Figure 4:
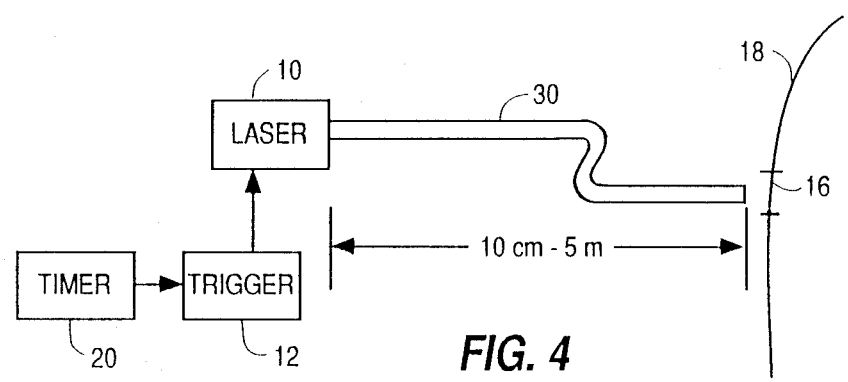
FIG. 4 is a schematic diagram of yet another system embodying features of the invention.

FIG. 4 illustrates another embodiment of the invention. Here, the laser 10, the trigger 12, and the timer 20, correspond to those shown in FIGS. 1 and 3. However, a transmitter in the form of a fiber-optic photoconductor 30 transmits the light along a flexible path to the target area 16.

Figure 5:
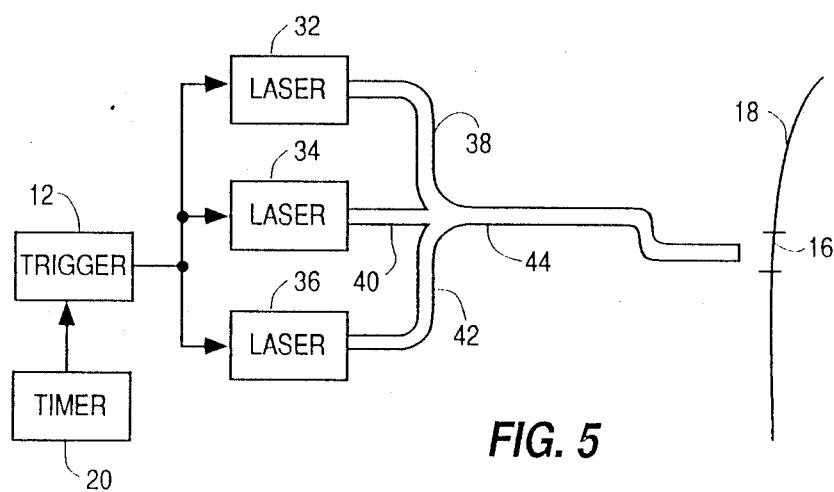
FIG. 5 is a schematic diagram of yet another system embodying features of the invention.

In FIG. 5 three lasers 32, 34, and 36 each corresponding to the laser 10 respond to the trigger 12 and the timer 20 at the same time. Fiber-optic light conductors in the form of optical fibers 38, 40, and 42 merge into a fiber-optic conductor 44 which forms a flexible path toward the target area 16.

In operation, laser 10 produces a single-frequency, light beam which is directed to the target area 16 of the creature, either directly, as shown FIG. 1, from the emergence area 14 or through the intermediate members 22, 24, 30, 38, 40, 42, and 44 as shown in FIGS. 3 to 5.

It has become apparent that the performance willingness of a horse can be increased especially by the radiation applied according to the invention. Applying a comparatively high output per unit area for a short duration affords several advantages.

First, the depth of penetration of the radiation is significantly increased. Therefor layers of tissue which have previously been inaccessible are also reached. Furthermore, for the enhancement of well-being, more favorable distribution of the kinds of radiation is achieved. The proportion of the electromagnetic radiation as well as the proportion of the photons is increased, the kind of the radiation generated also depending course, on the type of laser employed. While the photon statistic of a laser is already more advantageous for the desired effect than that of thermal light sources, it has turned out that the radiation, when using the method according to the invention, produces irritations in the tissue cells underneath the target area. These irritations are particularly conducive to achieving the desired purpose. The mechanical irritations have to be put down to phonons that are generated by energy gaps. This can be explained as detailed in the following:

The penetration photon possesses a certain intrinsic energy—by way of example 1.04 eV. Due to this energy, electrons of an atom or of a molecular are pumped to a higher level. This energetically more disadvantageous level remains in existence for only a very brief period of time; the electron returns to its normal level in individual bounds. The height of each individual bound corresponds to a specific frequency or energy and can be expressed in eV. Certain individual bounds lie within the wave range of sound, others within the wave range of electromagnetic radiation. The phonons and the electromagnetic radiation thus altogether stimulate the cell, which is what ensues in the desired effect.

Furthermore, of relevance is the short-duration application with high output which can be attained in an advantageous manner by using one laser unit only. Thereby all the cells below the target area are stimulated simultaneously, which intensifies the appropriate effect. On the whole it is thus possible to bring, by way of example, a horse during a period of regeneration following an injury having been suffered, to a peak performance within a comparatively short period of time.

A desired side effect results with respect to chronic ailments to which horses are subject to e.g. rheumatism or gout. The pains from these ailments are evidently felt less acutely or it is possible to almost eliminate them. Another side effect is that injuries to tissue obviously do heal better.

In addition, due to the enhanced well-being, the overall general condition of a living creature such as a horse is evidently improved, so that, possible ailments or injuries, if these exist, subside or abate more quickly.

If necessary, it is possible to conduct the laser beam originating from the laser light source through an optical system. It is also possible, however, to exploit the natural divergence of the laser beam in order to effect an adaptation to the size of the target area.

It is thus possible to couple the laser light source to a transmission means such as e.g. a photoconductor or a fiber-optical photoconductor, it also being possible for the transmission means to be constructed in a flexible fashion. Furthermore, it is possible to combine several laser light sources into a fiber-optical photoconductor when small emergence areas are desired, which is especially advantageous in the case of small target areas, so, that, for instance, a very small emergence areas is obtained when a light-conductive fiber having a diameter of 0.3 mm is employed. The utilization of flexible transmission means, particularly those with small emergence areas, affords the advantage that target areas in deep-seated body cavities can be reached with it being necessary to have to bring the living creature in question into special positions as well as that, due to the flexible transmission elements, all points of the body are reached.

By way of example a target area having an edge length of 10 mm and which can be radiated with a laser from a distance of 2.5 m has turned out to be favorable. The distance of the laser light source from the target area ranges from a few millimeters to 5 meters.

A further advantage consists in that, due to the short-duration effect of the laser radiation on the target area, no tissue changes are given rise to. On the contrary, a plurality of cells are simultaneously mechanically irritated, which results in that in all cases a defensive reaction to the mechanical irritation takes place in a uniform fashion. This again is conducive to the well-being of the horse.

In an experimental arrangement a laser having an output of 100 W was employed. This was triggered for extremely short durations, the triggering current pulse possessing a duration of only 10 to 12 ns. The laser had an emergence area of $0.3 \times 0.3$ mm$^2$. The target area was set to 10 mm $\times$ 10 mm at a distance of 2.5 m between the laser light source and the target area via an optical system with a convex lens. The radiation was distributed completely uniformly within the target area. Horses treated in this manner, especially those which had previously been suffering from pains, evidently felt better because their performance distinctly exceeded expectations. The exposure duration lasted approximately 1 to 2 minutes and the treatment was carried out once or twice daily. In addition, it proved possible, due to the improvement in the well-being or on account of the pain alleviation, to substantially shorten the period of regeneration. The photon wave length used was 904 nm or 1.04 eV. In this case, the one-minute effect of the radiation on the target area did not lead to any appreciable rise in temperature at the point in question.

The treatment method may also be applied three times daily for 30 seconds to 4 minutes.

The invention can be employed particularly advantageously at racecourses. In particular it is possible for the horse owners themselves to use the invention subsequent to having been suitably instructed—its use is thus not restricted to veterinarians only.

As shown in FIGS. 1 and 2, the distance between the laser 10 and the target area 16 may vary from 2 to 5 meters depending on the circumstances. The distance in FIG. 1 depends especially upon the divergence of the laser beam. The optical fibers 30 and 44 may vary from 10 cm. to 5 meters in length.

What is claimed is:

1. A therapeutic method for the body of a horse, comprising:
    irradiating a target area on the body of a horse with a source of laser light having a wavelength of approximately 904 nm,
    limiting the radiation dosage by triggering the source for approximately 10 ns to 15 ns to produce emission of the light
    controlling the area over which the source irradiates the area with an optical system that forms a 10 mm $\times$ 10 mm target area and controls the beam path length from a few mm to 5 m through an emergence area of 0.3 mm $\times$ 0.3 mm, and
    establishing the radiant power applied to the target to between 50 W and 350 W.

2. The method as in claim 1, wherein
the controlling includes directing the radiation through flexible optical directing means toward the target area on the body of the horse.

3. The method as in claim 1, wherein the controlling includes varying the size of the target area by varying the divergence of light from the laser source.

4. The method as in claim 1, wherein the controlling of the area includes forming the 10 mm × 10 mm target area at approximately 2.5 m from said source.

5. The method as in claim 1, wherein the limiting includes using the radiation dosage three times daily for 30 seconds to 4 minutes.

6. The method as in claim 1, wherein the controlling includes applying the irradiation to the target area from a single emergence area.

7. The method as in claim 6, wherein applying the irradiation to the target area from a single emergence area includes obtaining the irradiation from a single source of laser light.

8. The method as in claim 6, wherein irradiating the target from a single emergence area includes obtaining the irradiation from a plurality of sources of laser light whose outputs are combined to a single emergence region with flexible optical fibers.

* * * * *